United States Patent
Wood et al.

(10) Patent No.: US 8,377,955 B2
(45) Date of Patent: Feb. 19, 2013

(54) BRANCHED 3- AND 6-SUBSTITUTED QUINOLINES AS CGRP RECEPTORS ANTAGONISTS

(75) Inventors: Michael R. Wood, Brentwood, TN (US); June J. Kim, Brookline, MA (US); Kathy Schirripa, Quakertown, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 250 days.

(21) Appl. No.: 12/997,033

(22) PCT Filed: Jun. 3, 2009

(86) PCT No.: PCT/US2009/046107
§ 371 (c)(1),
(2), (4) Date: Dec. 9, 2010

(87) PCT Pub. No.: WO2009/152010
PCT Pub. Date: Dec. 17, 2009

(65) Prior Publication Data
US 2011/0105549 A1    May 5, 2011

Related U.S. Application Data

(60) Provisional application No. 61/131,808, filed on Jun. 12, 2008.

(51) Int. Cl.
*A61K 31/473* (2006.01)
*C07D 471/20* (2006.01)

(52) U.S. Cl. .............................. 514/278; 546/15; 546/48
(58) Field of Classification Search ................. 514/278; 546/15, 48
See application file for complete search history.

(56) References Cited

U.S. PATENT DOCUMENTS

| 7,696,192 B2 | 4/2010 | Bell et al. |
| 2009/0239870 A1 | 9/2009 | Bell et al. |
| 2009/0247514 A1 | 10/2009 | Bell et al. |
| 2010/0160334 A1 | 6/2010 | Bell et al. |

FOREIGN PATENT DOCUMENTS

| WO | 2006031491 | 3/2006 |
| WO | 2007061676 | 5/2007 |
| WO | 2007061677 | 5/2007 |

OTHER PUBLICATIONS

PCT International Search Report dated Feb. 2, 2010, for related International Applicaiton No. PCT/US2009/046107; 2 pages.
PCT Written Opinion dated Feb. 2, 2010, for related International Application No. PCT/US2009/046107; 2 pages.

*Primary Examiner* — Charanjit Aulakh
(74) *Attorney, Agent, or Firm* — Nicole M. Beeler; Gerard M. Devlin

(57) ABSTRACT

The present invention is directed to novel branched 3- and 6-substituted quinoline derivatives which are antagonists of CGRP receptors and useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

19 Claims, No Drawings

BRANCHED 3- AND 6-SUBSTITUTED QUINOLINES AS CGRP RECEPTORS ANTAGONISTS

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP (8-37), a peptide CGRP antagonist (Williamson et al., Cephalalgia, 1997, 17, 525-531). Trigeminal ganglion stimulation increased facial blood flow in the rat, which was inhibited by CGRP (8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Dodds et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4 (4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4 (4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189 (3), 225); inflammatory bowel disease, irritable bowel syndrome, (Hoffman et al. Scandinavian Journal of Gastroenterology, 2002, 37 (4) 414-422) and cystitis. Of particular importance is the acute or prophylactic treatment of headache, including migraine and cluster headache.

The present invention relates to novel branched 3- and 6-substituted quinoline derivatives that are useful as ligands for CGRP receptors, in particular antagonists for CGRP receptors, their use in therapy, pharmaceutical compositions comprising them and methods of therapy using them.

SUMMARY OF THE INVENTION

The present invention is directed to novel branched 3- and 6-substituted quinoline derivatives which are antagonists of CGRP receptors and useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The invention encompasses a genus of compounds of the formula I:

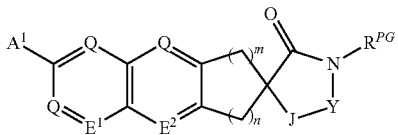

wherein:
$E^1$ and $E^2$ are independently selected from:
(1) =N—,
(2) =N$^+$(O$^-$)—, and
(3) =C(R$^5$)—
wherein at least one of $E^1$ and $E^2$ must be selected to contain nitrogen;
each Q is independently selected from:
(1) =N—,
(2) =N$^+$(O$^-$)—, and
(3) =C(R$^5$)—;
$A^1$ is selected from:

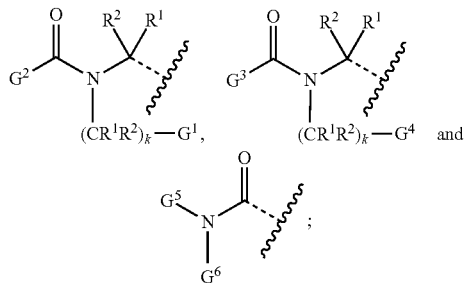

wherein when k=0, this represents a bond between nitrogen and $G^1$ or $G^4$;
$R^1$ and $R^2$ are each independently selected from:
(1) hydrogen,
(2) $C_{1-6}$ alkyl, which is unsubstituted or substituted with 1-5 substituents each independently selected from:
(a) —$C_{3-6}$cycloalkyl, which is unsubstituted or substituted with 1-5 halo,
(b) —OR$^a$,
(c) —CO$_2$R$^a$,
(d) halo and,
(e) phenyl, which is unsubstituted or substituted with 1-5 halo,
(3) halo, and
(4) phenyl or pyridinyl, which is unsubstituted or substituted with 1-5 substituents each independently selected from:
(a) halo,
(b) —OR$^a$,
(c) —CN, and
(d) —$C_{1-6}$alkyl, which is unsubstituted or substituted with 1-5 halo;

each R$^5$ is independently selected from:
(1) hydrogen
(2) —$C_{1-6}$alkyl, which is unsubstituted or substituted with 1-6 halo,
(3) halo,
(4) —OR$^a$, and
(5) —CN;
$G^1$ is selected from:
(1) oxatanyl, tetrahydropyranyl, tetrahydrothiapyranyl and tetrahydrothienyl, which is unsubstituted or substituted with 1-5 substituents independently selected from R$^3$, R$^4$, R$^6$, R$^7$ and R$^8$, and
(2) pyrrolidinyl, which is substituted with —CO$_2$R$^a$, and optionally substituted with 1-3 groups independently selected from:
(a) phenyl,
(b) OR$^a$,
(c) halo,
(d) —CN, and
(e) —$C_{1-6}$alkyl, which is unsubstituted or substituted with 1-5 halo;
$G^2$ is selected from:
(1) hydrogen,
(2) —$C_{1-6}$alkyl, which is unsubstituted or substituted with 1-6 substituents, substituents each independently selected from:
(a) halo,
(b) hydroxy,
(c) —O—$C_{1-6}$alkyl, which is unsubstituted or substituted with 1-5 halo,
(d) —$C_{3-6}$cycloalkyl,
(e) phenyl, which is unsubstituted or substituted with 1-5 substituents each independently selected from:
(i) —$C_{1-4}$alkyl,
(ii) —O—$C_{1-6}$alkyl,
(iii) halo,
(iv) trifluoromethyl, and
(v) —OCF$_3$,
(3) —$C_{3-6}$cycloalkyl, which is unsubstituted or substituted with 1-6 substituents, substituents each independently selected from:
(a) halo,
(b) hydroxyl,
(c) —O—$C_{1-6}$alkyl, which is unsubstituted or substituted with 1-5 halo,
(d) —$C_{1-6}$alkyl, which is unsubstituted or substituted with 1-5 halo, and
(e) phenyl,
(4) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
(a) halo,
(b) —$C_{1-6}$alkyl, which is unsubstituted or substituted with 1-5 halo,
(c) —O—$C_{1-6}$alkyl, which is unsubstituted or substituted with 1-5 halo,
(d) —$C_{3-6}$cycloalkyl,
(e) oxo, (f) —CN,
(g) hydroxyl and
(h) phenyl, and
(5) a group selected from $G^3$;
$G^3$ is selected from:
(1) tetrahydropyranyl, which is unsubstituted or substituted with 1-4 substitutents each independently selected from:
(a) halo,
(b) —$OR^a$,
(c) —$C_{1-6}$alkyl, which is unsubstituted or substituted with 1-5 halo,
(d) —$C_{3-6}$cycloalkyl,
(e) —$CO_2R^a$,
(f) oxo, and
(g) phenyl,
(2) —$C_{1-6}$alkyl which is optionally substituted with 1-5 halo, but which must be further substituted with 1-4 substitutents each independently selected from:
(a) —$SR^a$,
(b) —$S(O)_vR^d$,
(c) —$NR^aR^c$,
(d) —OBn, which is unsubstituted or substituted with 1-5 halo,
(e) —OC(=O)$R^a$,
(f) —$CO_2R^a$,
(g) —C(=O)$NR^bR^c$,
(h) —C(=O)$R^a$,
(i) —$C_{1-6}$alkyl-O—$C_{1-6}$alkyl-$OR^a$,
(j) —N($R^a$)—C(=O)$NR^bR^c$, and
(k) —N($R^a$)—$CO_2R^d$,
(3) piperidinyl or pyrrolidinyl which is substituted with 1-4 substituents each independently selected from:
(a) —C(=O)$R^a$,
(b) —OC(=O)$R^a$,
(c) —C(=O)$NR^bR^c$, and
(d) —$S(O)_vR^d$,
$G^4$ is selected from:
(1) $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzopyranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indazolyl, indolinyl, indolyl, isochromanyl, isoindolinyl, isoquinolinyl, isoxazolyl, isoxazolinyl, isoxazolidinyl, isothiazolidinyl, isothiazolyl, morpholinyl, naphthyridinyl, oxadiazolyl, oxazolyl, oxazolinyl, oxazolidinyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, phthalazinyl, piperidyl, piperazinyl, pyrazinyl, pyrazolidinyl, pyrazolyl, pyridazinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, triazolyl and triazolinyl, which is unsubstituted or substituted with 1-5 substituents independently selected from $R^3$, $R^4$, $R^6$, $R^7$ and $R^8$, and
(2) a group selected from $G^1$;

$G^5$ is selected from:
(1) —$C_{1-4}$alkyl-phenyl which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(f) —$S(O)_vR^d$, and
(g) —N($R^a$)$SO_2R^d$,
(2) —$C_{1-4}$alkyl-heterocycle wherein said heterocycle is selected from pyridyl, pyrimidinyl, and indazolyl, which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(f) —$S(O)_vR^d$, and
(g) —N($R^a$)$SO_2R^d$, and
(3) —$C_{1-4}$alkyl which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(f) —$S(O)_vR^d$, and
(g) —N($R^a$)$SO_2R^d$;
$G^6$ is selected from
(1) hydrogen,
(2) —$C_{1-6}$alkyl, which is unsubstituted or substituted with 1-5 groups independently selected from:
(a) halo,
(b) $OR^a$,
(c) —CN, and
(d) phenyl, which is unsubstituted or substituted with 1-5 halo, and
(3) —$C_{3-6}$cycloalkyl, which is unsubstituted or substituted with 1-5 groups independently selected from:
(a) halo,
(b) $OR^a$,
(c) —CN, and
(d) phenyl, which is unsubstituted or substituted with 1-5 halo;
$R^3$, $R^4$, $R^6$, $R^7$ and $R^8$ are each independently selected from:
(1) hydrogen,
(2) —$C_{1-6}$alkyl, which is unsubstituted or substituted with 1-5 substituents each independently selected from:
(a) halo,
(b) —$OR^a$,
(c) —$C_{3-6}$cycloalkyl,
(d) phenyl or heterocycle, wherein said heterocycle is selected from: benzodioxolyl, imidazolyl, indoolyl, pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from
(i) halo,
(ii) —$C_{1-6}$alkyl, which is unsubstituted or substituted with 1-5 halo, and
(iii) —$OR^a$,
(e) —$CO_2R^a$, (f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(3) —C$_{3-6}$cycloalkyl, which is unsubstituted or substituted with 1-5 substituents each independently selected from:
  (a) halo,
  (b) —CN,
  (c) —C$_{1-6}$alkyl, which is unsubstituted or substituted with 1-5 halo,
  (d) —OR$^a$, and
  (e) phenyl, which is unsubstituted or substituted with 1-5 substituents each independently selected from:
    (i) —OR$^a$,
    (ii) halo,
    (iii) —CN, and
    (iv) —C$_{1-6}$alkyl, which is unsubstituted or substituted with 1-5 halo,
(4) phenyl or heterocycle, wherein said heterocycle is selected from: benzimidazolyl, benzoxazolyl, indanyl, indolyl, morpholinyl, oxadiazolyl, oxazolyl, pyridyl, pyrimidinyl, pyrazinyl, pyrazolyl, pyridazinyl, piperidinyl, piperazinyl, pyrrolidinyl, thienyl, tetrazolyl and thiazolyl, which phenyl or heterocycle is unsubstituted or substituted with 1-5 substituents each independently selected from:
  (a) halo,
  (b) —OR$^a$,
  (c) —C$_{3-6}$cycloalkyl,
  (d) phenyl or pyridyl, which is unsubstituted or substituted with 1-5 substituents each independently selected from:
    (i) halo,
    (ii) C$_{1-6}$alkyl, which is unsubstituted or substituted with 1-6 halo, and
    (iii) —OR$^a$,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —O—CO$_2$R$^d$,
  (m) —O—(C=O)—NR$^b$R$^c$,
  (n) —NR$^b$—(C=O)—NR$^b$R$^c$,
  (o) —C(=O)R$^a$, and
  (p) —C$_{1-6}$alkyl, which is unsubstituted or substituted with 1-6 halo,
(5) halo,
(6) oxo,
(7) —OR$^a$,
(8) —CN,
(9) —CO$_2$R$^a$,
(10) —C(=O)R$^a$,
(11) —NR$^b$R$^c$,
(12) —S(O)$_v$R$^d$,
(13) —C(=O)NR$^b$R$^c$,
(14) —O—(C=O)R$^a$,
(15) —O—CO$_2$R$^d$,
(16) —N(R$^b$)CO$_2$R$^d$,
(17) —O—(C=O)—NR$^b$R$^c$,
(18) —NR$^b$—(C=O)—NR$^b$R$^c$,
(19) —SO$_2$ NR$^b$R$^c$, and
(20) —N(R$^b$)SO$_2$R$^d$,
and R$^7$ and R$^8$ and the atom(s) to which they are attached may join to form a ring selected from azetidinyl, aziridinyl, cyclobutyl, cycloheptyl, cyclohexyl, cyclooctyl, cyclopentyl, cyclopropyl, dihydrobenzofuranyl, dihydrobenzopyranyl, dioxanyl, dioxoalanyl, indanyl, indenyl, indolinyl, isoindolinyl, morpholinyl, oxetanyl, piperazinyl, piperidinyl, pyrrolidinyl, tetrahydrofuranyl, tetrahydroisoquinolinyl, tetrahydronaphthyl, tetrahydroquinolinyl, tetrahydropyranyl, tetrahydrothiapyranyl, tetrahydrothienyl, thiamorpholinyl, and thietanyl, wherein the sulfur is optionally oxidized to the sulfone or sulfoxide, which ring is unsubstituted or substituted with 1-5 substituents each independently selected from:
  (a) —C$_{1-6}$alkyl, which is unsubstituted or substituted with 1-3 substituents each independently selected from:
    (i) halo,
    (ii) —OR$^a$,
    (iii) —C$_{3-6}$cycloalkyl,
    (iv) —CO$_2$R$^a$,
    (v) —NR$^b$R$^c$,
    (vi) —S(O)$_v$R$^d$,
    (vii) —C(=O)NR$^b$R$^c$, and
    (viii) phenyl, which is unsubstituted or substituted with 1-5 halo,
  (b) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-5 substituents each independently selected from:
    (i) halo,
    (ii) —C$_{1-6}$alkyl, which is unsubstituted or substituted with 1-5 halo, and
    (iii) —OR$^a$,
  (c) —OR$^a$,
  (d) halo,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —O—(C=O)R$^a$,
  (m) —O—CO$_2$R$^d$,
  (n) —O—(C=O)—NR$^b$R$^c$,
  (o) —NR$^b$—(C=O)—NR$^b$R$^c$,
  (p) —C(=O)R$^a$, and
  (q) oxo;
R$^{PG}$ is selected from:
(1) hydrogen,
(2) —C$_{1-6}$alkyl which is unsubstituted or substituted with 1-5 halo,
(3) —CH$_2$OR$^a$,
(4) —CH$_2$—O—CH$_2$CH$_2$Si(CH$_3$)$_3$,
(5) —(CH$_2$)$_k$-phenyl, which is unsubstituted or substituted with 1-3 substituents each independently selected from:
  (a) halo,
  (b) —OR$^a$, (c) —CN, and
(d) —$C_{1-6}$alkyl, which is unsubstituted or substituted with 1-6 halo;

J is selected from:
(1) =$C(R^{16a})$—,
(2) —$CR^{17}R^{18}$—,
(3) —C(=O)—, and
(4) —$N(R^b)$—;

Y is selected from:
(1) =$C(R^{16b})$—,
(2) —$CR^{17}R^{18}$—,
(3) —C(=O)—,
(4) =N—, and
(5) —$N(R^{16b})$—;

$R^{17}$ and $R^{18}$ are each independently selected from:
(1) hydrogen,
(2) halo,
(3) —$OR^a$,
(4) —$C_{1-6}$alkyl, which is unsubstituted or substituted with 1-4 substituents each independently selected from:
  (a) halo,
  (b) —$OR^a$,
  (c) —CN,
  (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
    (i) —$OR^a$,
    (ii) halo,
    (iii) —CN,
    (iv) —$C_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (a) halo,
  (b) —CN,
  (c) —$OR^a$,
  (d) nitro,
  (e) —$C_{1-6}$alkyl which is unsubstituted or substituted with 1-6 halo;

and $R^{17}$ and $R^{18}$ and the atom to which they are attached may join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  (a) halo,
  (b) —$OR^a$,
  (c) —$C_{1-6}$alkyl, which is unsubstituted or substituted with 1-6 halo, and
  (d) phenyl, which is unsubstituted or substituted with 1-6 halo;

$R^{16a}$ and $R^{16b}$ are each independently selected from:
(1) hydrogen,
(2) —$C_{1-4}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
    (i) halo,
    (ii) —$OR^a$,
    (iii) —CN, and
    (iv) which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  (a) halo,
  (b) —$OR^a$,
  (c) —$C_{3-6}$cycloalkyl,
  (d) —$C_{1-4}$alkyl which is unsubstituted or substituted with 1-6 halo, and
  (e) phenyl, which is unsubstituted or substituted with 1-5 substituents each independently selected from:
    (i) halo,
    (ii) —$C_{1-6}$alkyl, which is unsubstituted or substituted with 1-6 halo, and
    (iii) —$OR^a$,
(4) halo,
(5) —$OR^a$,
(6) —CN,
(7) —$CO_2R^a$,
(8) —$NR^bR^c$, and
(9) —C(=O)$NR^bR^c$;

and $R^{16a}$ and $R^{16b}$ and the atom(s) to which they are attached may join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$OR^a$,
      (II) halo,
      (III) —CN, and
      (IV) —$C_{1-6}$alkyl which is unsubstituted or substituted with 1-6 halo,
    (v) —$CO_2R^a$,
    (vi) —$NR^bR^c$,
    (vii) —$S(O)_vR^d$,
    (viii) —C(=O)$NR^bR^c$,
    (ix) —$N(R^b)CO_2R^a$, and
    (x) —$N(R^b)SO_2R^d$, (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
  (i) halo,
  (ii) —OR$^a$,
  (iii) —CN, and
  (iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxo, and
(o) —(NR$^b$)SO$_2$R$^d$;

each R$^a$ is independently selected from:
  (1) hydrogen,
  (2) C$_{1-6}$alkyl, which is unsubstituted or substituted with 1-7 substituents each independently selected from:
    (a) halo,
    (b) —O—C$_{1-6}$alkyl, which is unsubstituted or substituted with 1-6 halo,
    (c) hydroxyl,
    (d) —C(=O)—O—C$_{1-6}$alkyl, which is unsubstituted or substituted with 1-6 halo,
    (e) —CN, and
    (f) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—C$_{1-6}$alkyl, which is unsubstituted or substituted with 1-6 halo,
      (iii) —CN,
      (iv) nitro,
      (v) hydroxyl, and
      (vi) —C$_{1-6}$alkyl, which is unsubstituted or substituted with 1-6 halo,
  (3) phenyl or heterocycle wherein said heterocycle is selected from pyridyl, indolyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —CN,
    (c) —O—C$_{1-6}$alkyl, which is unsubstituted or substituted with 1-6 halo,
    (d) nitro,
    (e) hydroxyl, and
    (f) —C$_{1-6}$alkyl, which is unsubstituted or substituted with 1-6 halo, and
  (4) —C$_{3-6}$cycloalkyl, which is unsubstituted or substituted with 1-6 halo;

R$^b$ and R$^c$ are each independently selected from:
  (1) hydrogen,
  (2) C$_{1-6}$alkyl, which is unsubstituted or substituted with 1-7 substituents each independently selected from:
    (a) halo,
    (b) —OR$^a$,
    (c) —CN,
    (d) —CO$_2$R$^a$,
    (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —OR$^a$,
      (iii) —C$_{1-6}$alkyl, which is unsubstituted or substituted with 1-6 halo, and
      (iv) nitro,
  (3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —C$_{1-6}$alkyl, which is unsubstituted or substituted with 1-6 halo,
    (d) —C$_{3-6}$cycloalkyl, which is unsubstituted or substituted with 1-6 halo,
    (e) —CN, and
    (f) —CO$_2$R$^a$,
  (4) —C$_{3-6}$cycloalkyl, which is unsubstituted or substituted with 1-6 halo; and R$^b$ and R$^c$ and the nitrogen to which they are attached may join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
    (a) halo,
    (b) —OR$^a$, and
    (c) —C$_{1-6}$alkyl, which is unsubstituted or substituted with 1-6 halo, and
    (d) phenyl;

each R$^d$ is independently selected from:
  (1) C$_{1-6}$alkyl, which is unsubstituted or substituted with 1-7 substituents each independently selected from:
    (a) halo,
    (b) —OR$^a$,
    (c) —CO$_2$R$^a$
    (d) —CN, and
    (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —OR$^a$,
      (iii) —CN,
      (iv) nitro, and
      (v) —C$_{1-6}$alkyl, which is unsubstituted or substituted with 1-6 halo, (2) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo,
(e) nitro,
(f) —CN, and
(g) —CO$_2$R$^a$,
(3) —C$_{3-6}$cycloalkyl, which is unsubstituted or substituted with 1-6 halo;
m is 1, 2, or 3;
n is 1, 2, or 3;
v is 0, 1, or 2;
k is 0, 1, or 2;
and pharmaceutically acceptable salts thereof.

Within the genus, the invention encompasses a first sub-genus of compounds of Formula I wherein m is 1 and n is 1.

Also within the genus, the invention encompasses a second sub-genus of compounds of formula Ia

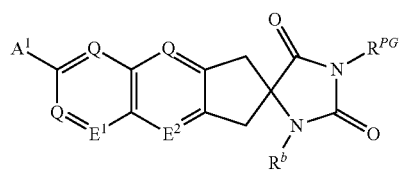

and pharmaceutically acceptable salts thereof.

Also within the genus, the invention encompasses a third sub-genus of compounds of formula Ib

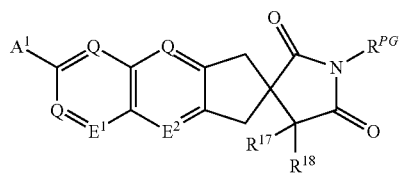

and pharmaceutically acceptable salts thereof.

Also within the genus, the invention encompasses a fourth sub-genus of compounds of formula Ic

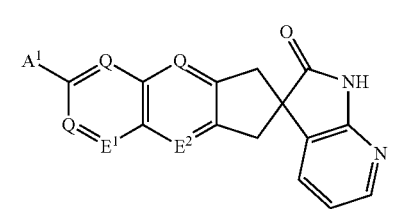

and pharmaceutically acceptable salts thereof.

Also within the genus, the invention encompasses a fifth sub-genus of compounds of formula Id

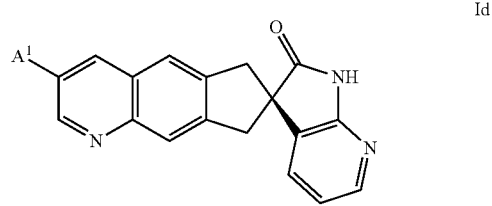

and pharmaceutically acceptable salts thereof.

Within the fifth sub-genus, the invention encompasses a first class of compounds of Formula Id wherein A$^1$ is

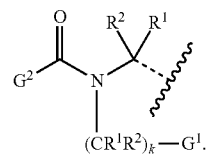

Also within the fifth sub-genus, the invention encompasses a second class of compounds of Formula Id wherein A$^1$ is

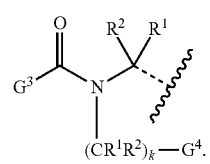

Also within the fifth sub-genus, the invention encompasses a third class of compounds of Formula Id wherein A$^1$ is

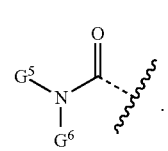

Also within the genus, the invention encompasses a sixth sub-genus of compounds of formula Ie

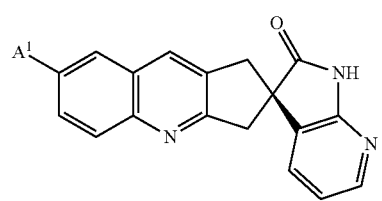

and pharmaceutically acceptable salts thereof.

Within the sixth sub-genus, the invention encompasses a fourth class of compounds of Formula Ie wherein A¹ is

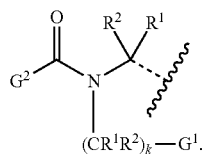

Also within the sixth sub-genus, the invention encompasses a fifth class of compounds of Formula Ic wherein A¹ is

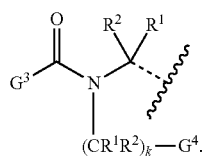

Also within the sixth sub-genus, the invention encompasses a sixth class of compounds of Formula Ie wherein A¹ is

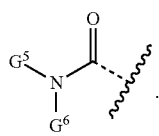

The invention also encompasses any of the examples that follow and pharmaceutically acceptable salts thereof.

The invention also encompasses a pharmaceutical composition which comprises an inert carrier and the compound of formula I.

The invention also encompasses a method for antagonism of CGRP receptor activity in a mammal which comprises the administration of an effective amount of the compound of formula I.

The invention also encompasses a method for treating, controlling, ameliorating or reducing the risk of headache, migraine or cluster headache in a mammalian patient in need of such which comprises administering to the patient a therapeutically effective amount of the compound of formula I.

The invention also encompasses a method of treating or preventing migraine headaches, cluster headaches, and headaches, said method comprising the co-administration, to a person in need of such treatment, of: a therapeutically effective amount of the compound of formula I or a pharmaceutically acceptable salt thereof; and a therapeutically effective amount of a second agent selected from serotonin agonists, analgesics, anti-inflamatory agents, anti-hypertensives and anticonvulsants.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Some of the compounds described herein contain olefinic double bonds, and unless specified otherwise, are meant to include both E and Z geometric isomers.

The present invention includes compounds of formula I wherein one or more hydrogen atoms are replaced by deuterium.

Tautomers of compounds defined in Formula I are also included within the scope of the present invention. For example, compounds including carbonyl —CH₂C(=O)— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which forms a ring of three or more atoms. "Cycloalkyl" include mono-, bi- or tri-cyclic structures, including bridged structures such as adamantanyl. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 4- to 8-membered monocyclic- or stable 8- to 12-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiomorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The variables set forth in the generic descriptions that appear multiple times are independently selected from the indicated groups. For example, $A^1$ and $A^5$ both include —S(O)$_v$— in their definitions and v is defined as 0, 1 or 2. Thus, $A^1$ can be —S(O)$_1$— and $A^5$ can be —S(O)$_2$—. The variable v is not required to be the same in both instances.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the Wails "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 μg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 μL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (PBS), 100 units/mL penicillin and 100 μg/mL streptomycin, and maintained at 37° C. and 95% humidity. Cells were subcultured by treatment with 0.25% trypsin with 0.1% EDTA in HBSS. Stable cell line generation was accomplished by co-transfecting 10 μg of DNA with 30 μg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 μg/mL hygromycin and 1 μg/mL puromycin) was added the following day. A clonal cell line was generated by single cell deposition utilizing a FACS Vantage SE (Becton Dickinson). Growth medium was adjusted to 150 μg/mL hygromycin and 0.5 μg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 μg of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)nH}$$

$$+ \frac{(Y_{max} - Y_{min})(\% \, I_{max} - \% \, I_{min}/100)}{}$$

Where Y is observed CPM bound, Y$_{max}$ is total bound counts, Y$_{min}$ is non specific bound counts, (Y$_{max}$-Y$_{min}$) is specific bound counts, % I$_{max}$ is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C.

and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, Examples 1 to 37 were tested and demonstrated activity as antagonists of the CGRP receptor in one or more of the aforementioned assays, generally with a $K_1$ or $IC_{50}$ value of less than about 50 µM. Such a result is indicative of the intrinsic activity of the compounds in use as antagonists of CGRP receptors. Representative data for selected compounds is included with the Examples.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a $5\text{-HT}_{1B/1D}$ agonist, for example sumatriptan, naratriptan, zolmitriptan, eletriptan, almotriptan, frovatriptan, donitriptan, and rizatriptan, a $5\text{-HT}_{1D}$ agonist such as PNU-142633 and a $5\text{-HT}_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant and fosaprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; an endothelin antagonist; a norepinephrin precursor; anti-anxiety agents such as diazepam, alprazolam, chlordiazepoxide and chlorazepate; serotonin $5HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particular embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

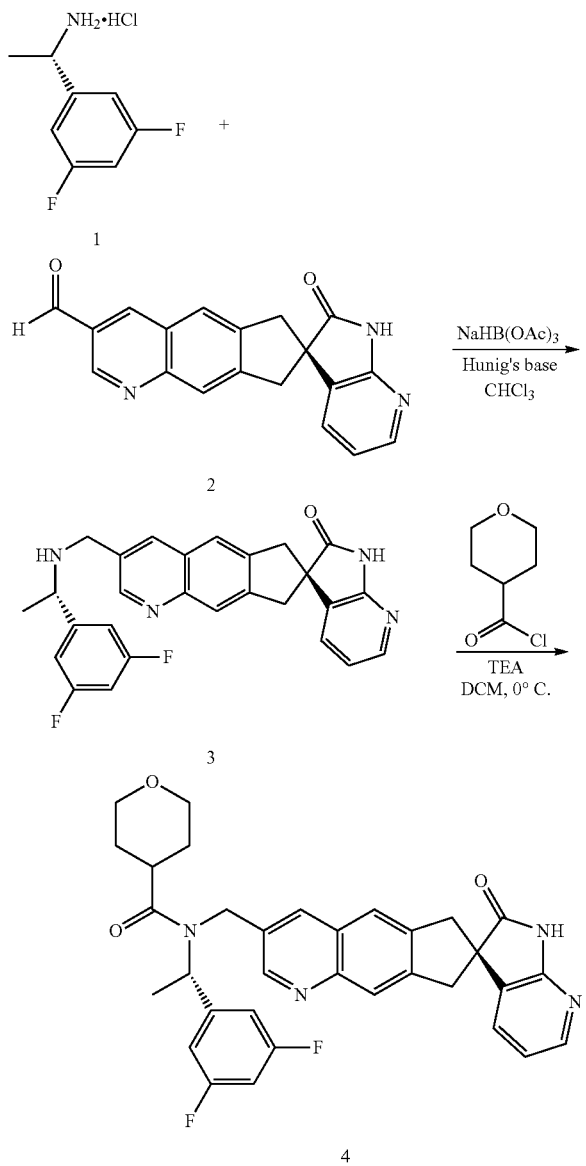

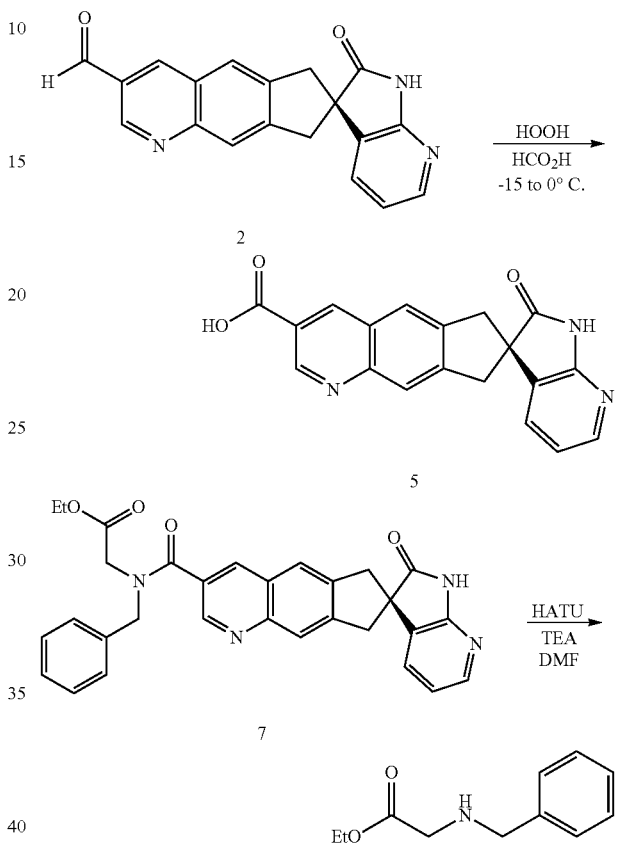

According to Scheme 1, amine 1 can be reductively alkylated with aldehyde 2 (Intermediate 1), in chloroform, using sodium triacetoxyborohydride and triethylamine to yield secondary amine 3. This amine can then be acylated with a variety of acid chlorides, in this case tetrahydro-2H-pyran-4-carbonyl chloride, using triethylamine as base, in DCM, to provide the claimed compound 4. Alternatively, Intermediate 3 can undergo similar transformations to yield compounds of the present invention.

Aldehyde 2 (Intermediate 1) can be oxidized to the carboxylic acid 5, using hydrogen peroxide (30% wt), in formic acid, at reduced temperatures −20 to 0° C. This acid can then be peptide coupled to amine 6, using HATU (N-[(dimethylamino)(3H-[1,2,3]triazolo[4,5-b]pyridin-3-yloxy)methylene]-N-methylmethanaminium hexafluorophosphate) and triethylamine, in DMF to provide the claimed compound 7.

The methodology shown in these schemes is not meant to limit the scope of the invention, but only to give representative examples and intermediates. Related intermediates and examples bearing a variety of substituents may be prepared by employing appropriately substituted starting materials or by derivatization of any intermediates and/or final products as desired by methods known in the art. Resolutions may be affected by other methodologies, such as fractional crystallization or diastereomeric salts, and it may be carried out on other synthetic intermediates or on the final products. Alternatively, an asymmetric synthesis of a key intermediate could be used to provide an enantiomerically enriched final product.

Of more general scope are the structures appearing in the following schemes, which describe in more general terms methods, reagents and conditions which may be used to prepare compounds of the present invention.

SCHEME 3

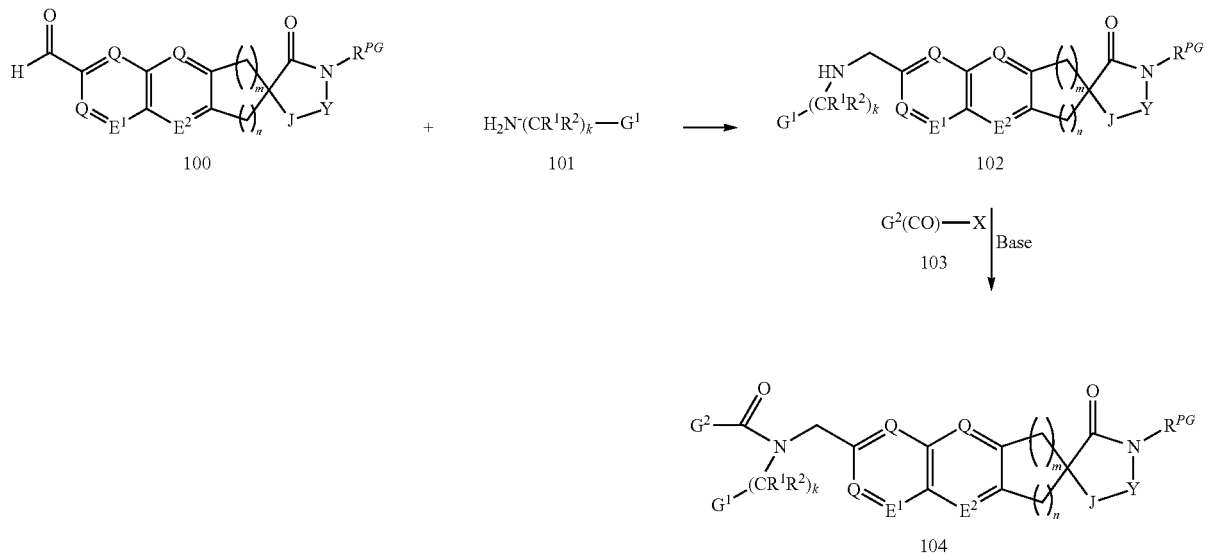

Scheme 3 shows how aldehyde 100, can reductively alkylate amines of general structure 101, using an appropriate reductant, such as NaHB(OAc)$_3$ or sodium cyanoborohydride, in a solvent such as DCE, chloroform or DCM, either in the presence or absence of a general acid catalyst, such as HOAc, to give the secondary amines 102. Acylation of 102 with various electrophiles of general structure 103 (acid halides: X=F, Cl, Br, or I; active esters: X=HOBt, HOAt, etc.) can be accomplished using a base, such as triethylamine, as needed, in an appropriate solvent such as DMF or DCM, giving claimed compounds 104. Similarly, Scheme 11 shows how a different set of claimed compounds (108) can be prepared in an analogous manner.

SCHEME 4

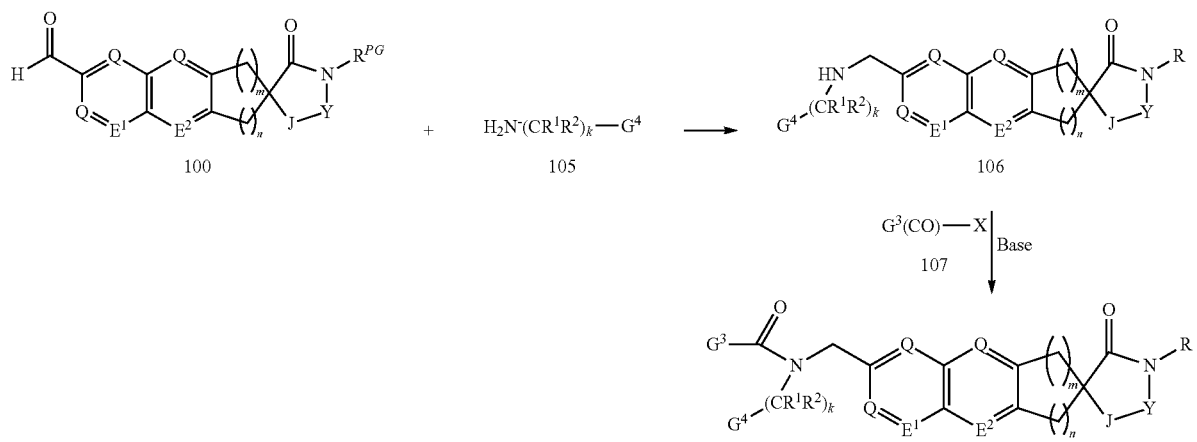

Alternatively, according to Scheme 4, aldehyde 100, can be oxidized with an appropriate oxidant, such as hydrogen peroxide, in an appropriate solvent, such as aqueous formic acid, at a temperature ranging from −50 to 30° C. to give the carboxylic acid 109. This acid can be peptide coupled to various amines of general structure 110, under standard peptide coupling conditions, such as HATU or EDCI/HOBt, in the presence of a base, such as triethylamine, as needed, in a solvent such as DMF or DCM, to give the claimed compounds 111.

SCHEME 5

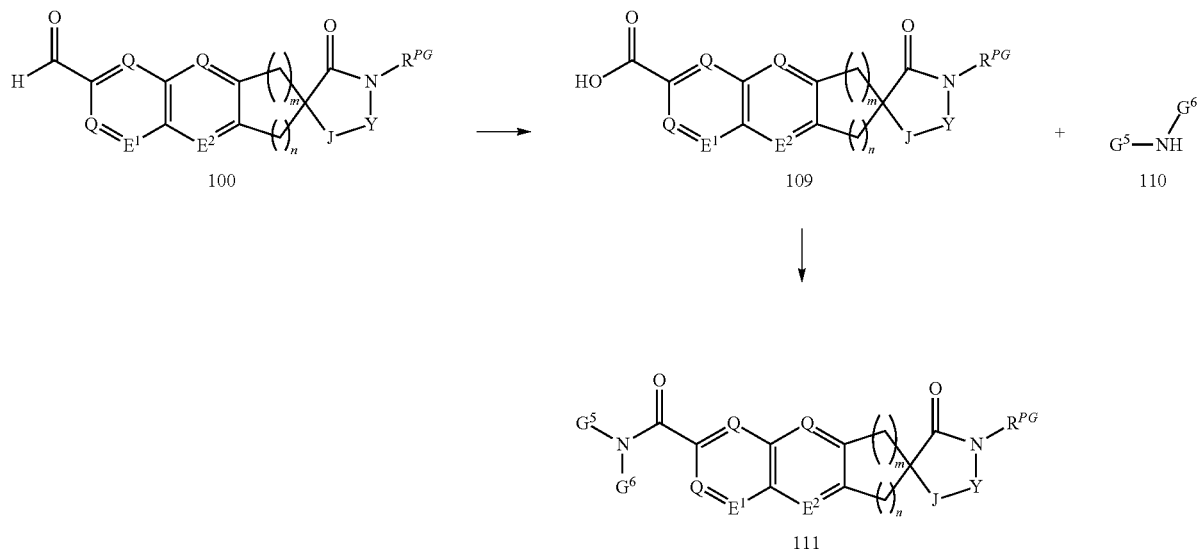

Simple modifications of these routes, including different protecting group strategies, application of well-precedented methodology, and the use of starting materials and reagents other than those described in the forgoing schemes, may be used to provide other intermediates and claimed compounds.

In some cases the final product may be further modified, for example, by manipulation of substituents. These manipulation my include, but are not limited to, reduction, oxidation, alkylation, acylation, and hydrolysis reaction which are commonly known to those skilled in the art.

In some cases the order of carrying out the foregoing reactions schemes may be varied to facilitate the reaction or to avoid unwanted reaction products. The following examples are provided so that the invention might be more fully understood. These example are illustrative only and should not be construed as limiting the invention in any way.

INTERMEDIATE 1

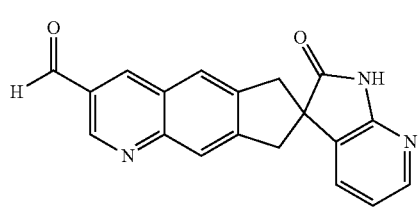

2'-Oxo-1',2',6,8-tetrahydrospiro[cyclopenta[g]quinoline-7,3'-pyrrolo[2,3-b]pyridine]-3-carbaldehyde Title compound was prepared according to known literature (Bell, I. M., et al. WO 2007/061677 A2 20070531) methods, affording either enantiomer or a racemic mix as needed.

INTERMEDIATE 2

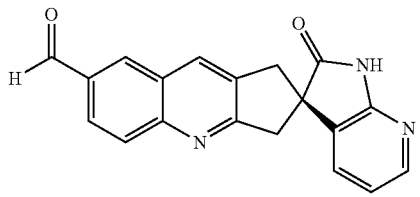

(2S)-2'-oxo-1,1',2',3-tetrahydrospiro[cyclopenta[b]quinoline-2,3'-pyrrolo[2,3-b]pyridine]-7-carbaldehyde Step A. 1-{[2-(Trimethylsilyl)ethoxy]methyl}-1H-pyrrolo[2,3-b]pyridine Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step. C. 1-{[2-(Trimethylsiyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

Step D. 3,3-Diallyl-1-{[2-(trimethylsilyl)ethoxy]methyl}-1,3-dihydro-2H-pyrrolo[2,3-b]pyridin-2-one To a solution of 1-{[2-(trimethylsilyl)ethoxy]methyl}-1,3-dihydro-2H-pyrrolo[2,3-b]pyridin-2-one from Step C (1.00 g, 3.78 mmol) and cesium carbonate (3.70 g, 1.4 mmol) in DMF (10 mL) was added a solution of allyl bromide (0.720 mL, 8.32 mmol). After 6 h, the mixture was poured onto saturated $NaHCO_3$ (50 mL) and extracted with $CH_2Cl_2$ (3×30 mL). The combined organic layers were dried over $Na_2SO_4$, filtered, and concentrated in vacuo. The crude product was purified by silica gel chromatography, eluting with a gradient of hexane:EtOAc—100:0 to 50:50, to give the title compound. MS: m/z=345 (M+1).

Step E. 1'-{[2-(Trimethylsilyl)ethoxy]methyl}spiro[cyclopent-3-ene-1,3'-pyrrolo[2,3-b]pyridin]-2'(1'H)-one A mixture of 3,3-diallyl-1-{[2-(trimethylsilyl)ethoxy]methyl}-1,3-dihydro-2H-pyrrolo[2,3-b]pyridin-2-one from Step D (1.02 g, 2.96 mmol) and Grubbs second generation catalyst (37 mg, 0.045 mmol) in DCE (60 mL) was heated at reflux for 3.5 h. The mixture was concentrated in vacuo and purified by silica gel chromatography, eluting with a gradient of hexane:EtOAc—100:0 to 75:25, to give the title compound. MS: m/z=317 (M+1).

Step F. (1S)-1'-{[2-(Trimethylsilyl)ethoxy]methyl}-3H-spiro[cyclopentane-1,3'-pyrrolo[2,3-b]pyridine]-2',3(1'H)-dione Borane-methyl sulfide complex (0.984 mL, 1.97 mmol, 2M in THF) was added drop wise to a solution of 1'-{[2-(trimethylsilyl)ethoxy]methyl}spiro[cyclopent-3-ene-1,3'-pyrrolo[2,3-b]pyridin]-2'(1'H)-one from Step E (208 mg, 0.656 mmol) in THF (3 mL) at 0° C. and the solution was slowly warmed to RT over 3.5 h. The reaction mixture was carefully quenched by the slow addition of water until hydrogen evolution ceased and then concentrated in vacuo. The resulting solid was dissolved in DMF (1 mL) and DCE (0.5 mL) and added drop wise to a suspension of PDC (740 mg, 1.97 mmol) in DCE (5 mL) at ambient temperature. The reaction mixture was heated at 65° C. for 21 h, with additional PDC (500 mg) added after 18 h. Celite was added to the reaction mixture until clumping occurred, and then it was diluted with $t_2O$ (50 mL). The mixture was filtered through a Celite plug, rinsing with additional $Et_2O$ (4×50 mL) and the filtrate concentrated in vacuo. The crude product was purified by silica gel chromatography, eluting with a gradient of hexane:EtOAc—100:0 to 50:50. This racemic mixture was resolved using SFC, eluting with $CO_{2(l)}$/EtOH to give the title compound. MS: m/z=333 (M+1).

Step G. Methyl (2S)-2'-oxo-1'-{[2-(trimethylsilyl)ethoxy]methyl}-1,1',2',3-tetrahydrospiro[cyclopenta[b]quinoline-2,3'-pyrrolo[2,3-b]pyridine]-7-carboxylate To a solution of (1S)-1'-{[2-(trimethylsilyl)ethoxy]methyl}-3H-spiro[cyclopentane-1,3'-pyrrolo[2,3-b]pyridine]-2',3(1'H)-dione from step F (375 mg, 1.13 mmol) and methyl 4-amino-3-formylbenzoate (202 mg, 1.13 mmol) in MeOH (5 mL) was added piperidine (192 mg, 2.26 mmol). The mixture was then place into a 75° C. bath, open to the air, and allowed to boil dry. Reaction progress was occasionally checked by adding MeOH (~3 mL) prior to removal of an aliquot for LCMS analysis. After heating for 22 hours, the reaction was allowed to cool before being diluted with DCM (minimal amount) and applied directly to a silica gel column, eluting with a gradient of hexane:EtOAc—80:20 to 30:70 (pausing at 60:40) to give the title compound. MS: m/z=476 (M+1).

Step H. (2S)-2'-Oxo-1'-{[2-(trimethylsilyl)ethoxy]methyl}-1,1',2',3-tetrahydrospiro[cyclopenta[b]quinoline-2,3'-pyrrolo[2,3-b]pyridine]-7-carbohydrazide To a solution of methyl (2S)-2'-oxo-1'-{[2-(trimethylsilyl)ethoxy]methyl}-1,1',2',3-tetrahydrospiro[cyclopenta[b]quinoline-2,3'-pyrrolo[2,3-b]pyridine]-7-carboxylate from Step G (317 mg, 0.667 mmol) in MeOH (1 mL) was added hydrazine (1.0 mL, 32 mmol). The reaction was sealed and then heated to 70° C. for 18 hours. After cooling to ambient temperature, the bulk of the solvent was removed in vacuo. The residue was diluted with DCM (50 mL) and water (20 mL). The organics were then successively washed with water, half-saturated brine and brine before being dried over sodium sulfate. The organics were then filtered, concentrated in vacuo to give the title compound. MS: m/z=476 (M+1).

Step I. (2S)-2'-Oxo-1'-{[2-(trimethylsiyl)ethoxy]methyl}-1,1',2',3-tetrahydrospiro[cyclopenta[b]quinoline-2,3'-pyrrolo[2,3-b]pyridine]-7-carbaldehyde To a rapidly stirred solution of (2S)-2'-oxo-1'-{[2-(trimethylsilyl)eth-oxy]methyl}-1,1',2',3-tetrahydrospiro[cyclopenta[b]quinoline-2,3'-pyrrolo[2,3-b]pyridine]-7-carbohydrazide from Step H (317 mg, 0.667 mmol) in DCM (6.8 mL) was added water (2.7 mL) plus concentrated aqueous $NH_4OH$ (0.6 mL) and lastly potassium ferricyanide (549 mg, 1.67 mmol). After 4.5 hours the reaction was diluted with water (20 mL) and DCM (40 mL). The aqueous layer was extracted once with DCM (20 mL). The combined organics were washed successively with water then half-saturated brine and then dried over sodium sulfate. The organics were then filtered, concentrated in vacuo, and applied to a silica gel column for purification, eluting with a gradient of $CH_2Cl_2$: MeOH—99:1 to 90:10. Clean product-containing fractions were pooled and concentrated in vacuo to give the title compound. MS: m/z=446 (M+1).

Step J. (2S)-2'-Oxo-1,1',2',3-tetrahydrospiro[cyclopenta[b]quinoline-2,3'-pyrrolo[2,3-b]pyridine]-7-carbaldehyde To a solution of (2S)-2'-oxo-1'-{[2-(trimethylsilyl)ethoxy]methyl}-1,1',2',3-tetrahydrospiro[cyclopenta[b]quinoline-2,3'-pyrrolo[2,3-b]pyridine]-7-carbaldehyde from Step I (142 mg, 0.320 mmol) in MeOH (17 mL) was introduced gaseous anhydrous hydrogen chloride by bubbling the gas through the solution until the MeOH was saturated and mildly warmed. This saturation with HCl was repeated once again after 3 hours then the sealed reaction was allowed to sit at ambient temperature for 19 hours. The solution was then purged with a stream of nitrogen for 20-30 minutes, before being concentrated in vacuo. MeOH (50 mL) was added, then removed in vacuo, repeating this addition/concentration twice to remove excess HCl. The residue was dissolved in MeOH (17 mL) prior to the addition of concentrated aqueous $NH_4OH$ (0.7 mL). After 20 minutes the MeOH was removed in vacuo, fresh MeOH (50 mL) was added then remove in vacuo to produce a residue. This residue was dissolved in water (1.35 mL) plus 4 drops on conc. $H_2SO_4$. This aqueous solution was transferred to an Erlenmeyer flask using water (3 mL) and 2 more drops of conc. $H_2SO_4$. Slow neutralization with aqueous NaOH (1 M, ~2.5 mL) provided a solid which was filtered, washed with water, air dried and vacuum dried to give the title compound. MS: m/z=316 (M+1).

INTERMEDIATE 3

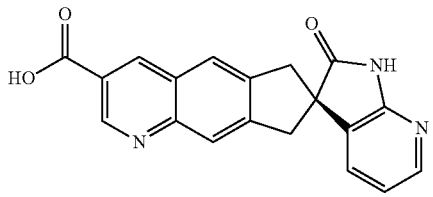

(7S)-2'-Oxo-1',2',6,8-tetrahydrospiro[cyclopenta[g]quinoline-7,3'-pyrrolo[2,3-b]pyridine]-3-carboxylic acid To a solution of (7S)-2'-oxo-1',2',6,8-tetrahydrospiro[cyclopenta[g]quinoline-7,3'-pyrrolo[2,3-b)]pyridine]-3-carbaldehyde (0.20 g, 0.634 mmol, Intermediate 1) in formic acid (0.36 mL), cooled to 0° C., was added hydrogen peroxide (0.158 mL, 30% aqueous solution, 1.903 mmol). This solution was sealed and kept at −15° C. for 5 days. The reaction was then diluted with water (5 mL) to induce precipitation. This precipitate was filtered to yield the title compound. MS: m/z=332 (M+1).

EXAMPLE 1

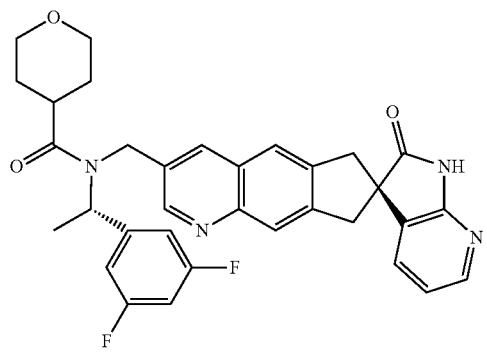 [SMILES: C[C@@H](c1cc(F)cc(F)c1)N(Cc1cnc2cc3c(cc2c1)C[C@@]1(C3)C(=O)Nc2ncccc21)C(=O)C1CCOCC1]

N-[(1R)-1-(3,5-Difluorophenyl)ethyl]-N-{[(7S)-2'-oxo-1',2',6,8-tetrahydrospiro-[cyclopenta[g]quinoline-7,3'-pyrrolo[2,3-b]pyridin]-3-yl]methyl}tetrahydro-2H-pyran-4-carboxamide Step A. (7S)-3-({[(1R)-1-(3,5-Difluorophenyl)ethyl]amino}methyl)-6,8-dihydrospiro[cyclopenta[g]quinoline-7,3'-pyrrolo[2,3-b]pyridin]-2'(1'H)-one To a stirred suspension of 2'-oxo-1',2',6,8-tetrahydrospiro[cyclopenta[g]quinoline-7,3'-pyrrolo[2,3-b]pyridine]-3-carbaldehyde (0.50 g, 1.6 mmol, Intermediate 1) and HOAc (192 µL, 3.33 mmol) in dry chloroform (5 mL) was added a solution of (1R)-1-(3,5-difluorophenyl)ethanamine hydrochloride (0.461 g, 2.38 mmol) and Hunig's base (0.415 mL, 2.38 mmol) in dry chloroform (2 mL). After 10 minutes, sodium triacetoxyborohydride (0.706 g, 3.33 mmol) was added. After 18 hours of stirring at ambient temperature, the mixture was diluted with DCM and saturated sodium bicarbonate. The layers were separated and the aqueous layer was extracted once with DCM. The combined organics were dried over sodium sulfate, filtered, and concentrated in vacuo to provide a residue. The residue was then was applied to a silica gel column for purification, eluting with a gradient of 1-10% methanol in DCM to give the title compound. MS: m/z=457 (M+1).

Step B. N-[(1R)-1-(3,5-Difluorophenyl)ethyl]-N-{[(7S)-2'-oxo-1',2',6,8-tetrahydrospiro[cyclopenta[g]quinoline-7,3'-pyrrolo[2,3-b]pyridin]-3-yl]methyl}tetrahydro-2H-pyran-4-carboxamide To a stirred solution of (7S)-3-({[(1R)-1-(3,5-difluorophenyl)ethyl]amino}methyl)-6,8-dihydrospiro[cyclopenta[g]quinoline-7,3'-pyrrolo[2,3-b]pyridin]-2'(1'H)-one from Step A (40 mg, 0.088 mmol) in DCM (1 mL), cooled to 0° C., were added tetrahydro-2H-pyran-4-carbonyl chloride (26 mg, 0.18 mmol) and triethylamine (31 µL, 0.22 mmol). The reaction was allowed to proceed at −15° C. for 18 h. The reaction was quenched with water and concentrated to give a residue, which was subjected to reverse phase chromatography eluting with a mixture of MeCN/water (0.1% TFA). The product-containing fractions were lyophilized to give the title compound as a TFA salt. Human CGRP receptor binding $K_i$=0.050 nM. MS: m/z=569 (M+1). HRMS: m/z=5692346; calculated m/z=569.2359 for $C_{33}H_{31}F_2N_4O_3$.

EXAMPLE 2

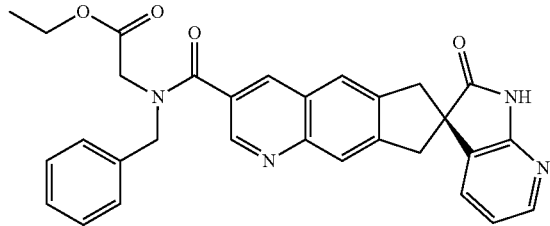 [SMILES: CCOC(=O)CN(Cc1ccccc1)C(=O)c1cnc2cc3c(cc2c1)C[C@@]1(C3)C(=O)Nc2ncccc21]

Ethyl(benzyl{[(7S)-2'-oxo-1',2',6,8-tetrahydrospiro[cyclopenta[g]quinoline-7,3'-pyrrolo[2,3-b]pyridin]-3-yl]carbonyl}amino)acetate Into a solution of (7S)-2'-oxo-1',2',6,8-tetrahydrospiro[cyclopenta[g]-quinoline-7,3'-pyrrolo[2,3-b]pyridine]-3-carboxylic acid (50 mg, 0.151 mmol, Intermediate 3) and N-benzylglycine ethyl ester (44.0 mg, 0.226 mmol) in DMF (2 mL) were added O-(7-azabenzotriazol-1-yl)-N,N,N',N'-tetramethyluronium hexafluoro-phosphate (86 mg, 0.226 mmol, HATU) and triethylamine (42 µL, 0.30 mmol). After 1 hour of stirring at ambient temperature, the solution was subjected to reverse phase chromatography eluting with a mixture of MeCN/water (0.1% TFA). The product-containing fractions were lyophilized to give the title compound as a TFA salt. MS: m/z=507 (M+1). Human CGRP receptor binding $K_i$=60 nM. HRMS: m/z=507.2040; calculated m/z=507.2027 for $C_{30}H_{27}N_4O_4$.

Essentially following analogous procedures to those outlined for Example 1 and using Intermediates 1 or 2 the following examples were prepared. The requisite starting materials were commercially available, described in the literature, or readily synthesized by one skilled in the art of organic synthesis. In some cases, straightforward protecting group strategies were applied, or chiral resolutions were performed.

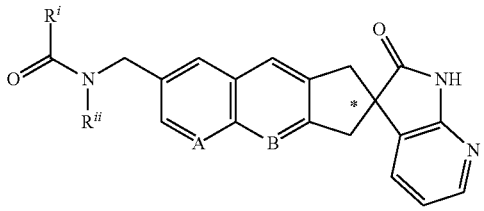

| Example # | $R^i$ | $R^{ii}$ | A | B | * | $K_i$ (nM) | LCMS (M + 1) |
|---|---|---|---|---|---|---|---|
| 3 | tetrahydro-2H-pyran-4-yl | (1R)-2,3-dihydro-1H-inden-1-yl | N | CH | S | | 545 |
| 4 | tetrahydro-2H-pyran-4-yl | (1R)-1-(3-chlorophenyl)ethyl | N | CH | S | 0.078 | 567 |
| 5 | tert-butyl | tetrahydro-2H-thiopyran-4-yl | N | CH | ± | | 501 |
| 6 | tetrahydro-2H-pyran-4-yl | cycloheptyl | N | CH | S | | 525 |
| 7 | tetrahydro-2H-pyran-4-yl | (1R)-1-(3,5-difluorophenyl)ethyl | N | CH | S | | 569 |
| 8 | tetrahydro-2H-pyran-4-yl | 3,5-dichlorobenzyl | N | CH | S | 4.6 | 587 |
| 9 | tetrahydro-2H-pyran-4-yl | 3-fluorobenzyl | N | CH | S | | 537 |
| 10 | tetrahydro-2H-pyran-2-yl | 3-fluorobenzyl | N | CH | S | 1.5 | 537 |
| 11 | 1-(acetyloxy)-1-methylethyl | (1R)-2,3-dihydro-1H-inden-1-yl | N | CH | S | | 561 |
| 12 | tert-butyl | tetrahydro-2H-pyran-4-yl | N | CH | S | 6.0 | 485 |
| 13 | (1S)-1-(benzyloxy)-2,2,2-trifluoro-1-methylethyl | | N | CH | S | 0.45 | 687 |
| 14 | (1S)-1-(benzyloxy)-2,2,2-trifluoro-1-methylethyl | (1R)-2,3-dihydro-1H-inden-1-yl | N | CH | S | | 663 |
| 15 | (1S)-1-(benzyloxy)-2,2,2-trifluoro-1-methylethyl | 3-fluorobenzyl | N | CH | S | | 655 |
| 16 | tetrahydro-2H-pyran-4-yl | [1-(tert-butoxycarbonyl)-4-phenylpyrrolidin-3-yl] | N | CH | S | 54 | 674 |
| 17 | 2-(methylthio)ethyl | 3-fluorobenzyl | N | CH | S | 1.6 | 527 |
| 18 | 2-thienylmethyl | 3-fluorobenzyl | N | CH | S | | 549 |
| 19 | 3-methoxy-3-oxopropyl | 3-fluorobenzyl | N | CH | S | | 539 |
| 20 | (2-methoxyethoxy)methyl | 3-fluorobenzyl | N | CH | S | | 541 |
| 21 | tetrahydro-2H-pyran-4-yl | cis-2-phenylcyclopentyl | N | CH | S | 0.12 | 573 |
| 22 | tetrahydro-2H-pyran-4-yl | trans-2-phenylcyclopentyl | N | CH | S | 0.098 | 573 |

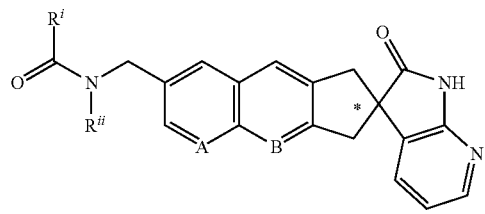

| Example # | $R^i$ | $R^{ii}$ | A | B | * | $K_i$ (nM) | LCMS (M + 1) |
|---|---|---|---|---|---|---|---|
| 23 | tetrahydro-2H-pyran-4-yl | cis-2-(4-chlorophenyl)cyclopentyl | N | CH | S | | 607 |
| 24 | 2-ethoxy-2-oxoethyl | 3-fluorobenzyl | N | CH | S | 1.2 | 539 |
| 25 | 1-(acetyloxy)ethyl | (1R)-2,3-dihydro-1H-inden-1-yl | N | CH | S | | 547 |
| 26 | 1-(acetyloxy)-1-methylethyl | (1R)-2,3-dihydro-1H-inden-1-yl | CH | N | ± | 0.075 | 561 |
| 27 | (dimethylamino)methyl | 3-fluorobenzyl | N | CH | S | 10 | 510 |
| 28 | tetrahydro-2H-pyran-4-yl | (1S,2S)-2-(benzyloxy)cyclopentyl | N | CH | S | | 603 |
| 29 | tetrahydro-2H-pyran-4-yl | (1R,2R)-2-(benzyloxy)cyclopentyl | N | CH | S | 0.41 | 603 |
| 30 | tetrahydro-2H-pyran-4-yl | 4-phenyl-pyrrolidin-3-yl | N | CH | S | 4.8 | 574 |
| 31 | 1-(acetyloxy)-1-methylethyl | (1R)-2,3-dihydro-1H-inden-1-yl | CH | N | S | 0.092 | 561 |

Essentially following analogous procedures to those outlined for Example 2 the following examples were prepared. The requisite starting materials were commercially available, described in the literature, or readily synthesized by one skilled in the art of organic synthesis. In some cases, straightforward protecting group strategies were applied, or chiral resolutions were performed.

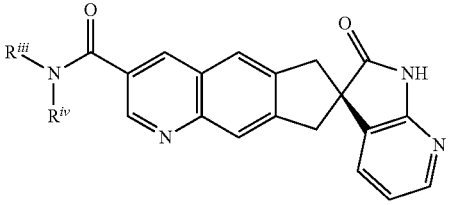

| Example # | $R^{iii}$ | $R^{iv}$ | $K_i$ (nM) | LCMS (M + 1) |
|---|---|---|---|---|
| 32 | 2-tert-butoxy-2-oxoethyl | Bn | | 535 |
| 33 | (1R)-2-tert-butoxy-2-oxo-1-phenylethyl | H | 120 | 521 |
| 34 | (1S)-2-tert-butoxy-2-oxo-1-phenylethyl | H | 140 | 521 |
| 35 | 2-methoxy-1-[(7-methyl-1H-indazol-5-yl)methyl]-2-oxoethyl | H | | 547 |
| 36 | 3-tert-butoxy-3-oxo-1-phenylpropyl | H | 76 | 535 |
| 37 | 1-benzyl-2-tert-butoxy-2-oxoethyl | H | | 535 |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diastereomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

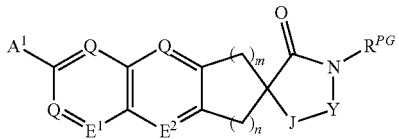

wherein:

E¹ and E² are independently selected from:
(1) =N—,
(2) =N⁺(O⁻)—, and
(3) =C(R⁵)— wherein at least one of E¹ and E² must be selected to contain nitrogen;

each Q is independently selected from:
(1) =N—,
(2) =N⁺(O⁻)—, and
(3) =C(R⁵)—;

A¹ is selected from:

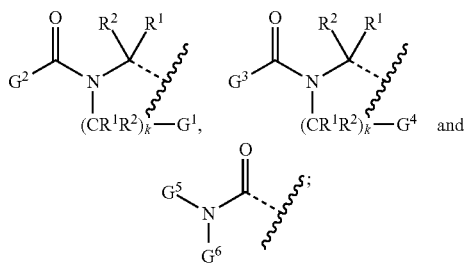

wherein when k=0, this represents a bond between nitrogen and G¹ or G⁴;

R¹ and R² are each independently selected from:
(1) hydrogen,
(2) $C_{1-6}$ alkyl, which is unsubstituted or substituted with 1-5 substituents each independently selected from:
  (a) —$C_{3-6}$cycloalkyl, which is unsubstituted or substituted with 1-5 halo,
  (b) —OR$^a$,
  (c) —CO$_2$R$^a$,
  (d) halo and,
  (e) phenyl, which is unsubstituted or substituted with 1-5 halo,
(3) halo, and
(4) phenyl or pyridinyl, which is unsubstituted or substituted with 1-5 substituents each independently selected from:
  (a) halo,
  (b) —OR$^a$,
  (c) —CN, and
  (d) —$C_{1-6}$alkyl, which is unsubstituted or substituted with 1-5 halo;

each R⁵ is independently selected from:
(1) hydrogen
(2) —$C_{1-6}$alkyl, which is unsubstituted or substituted with 1-6 halo,
(3) halo,
(4) —OR$^a$, and
(5) —CN;

G¹ is selected from:
(1) oxatanyl, tetrahydropyranyl, tetrahydrothiapyranyl and tetrahydrothienyl, which is unsubstituted or substituted with 1-5 substituents independently selected from R³, R⁴, R⁶, R⁷ and R⁸, and
(2) pyrrolidinyl, which is substituted with —CO$_2$R$^a$, and optionally substituted with 1-3 groups independently selected from:
  (a) phenyl,
  (b) OR$^a$,
  (c) halo,
  (d) —CN, and
  (e) —$C_{1-6}$alkyl, which is unsubstituted or substituted with 1-5 halo;

G² is selected from:
(1) hydrogen,
(2) —$C_{1-6}$alkyl, which is unsubstituted or substituted with 1-6 substituents, substituents each independently selected from:
  (a) halo,
  (b) hydroxy,
  (c) —O—$C_{1-6}$alkyl, which is unsubstituted or substituted with 1-5 halo,
  (d) —$C_{3-6}$cycloalkyl,
  (e) phenyl, which is unsubstituted or substituted with 1-5 substituents each independently selected from:
    (i) —$C_{1-4}$alkyl,
    (ii) —O—$C_{1-6}$alkyl,
    (iii) halo,
    (iv) trifluoromethyl, and
    (v) —OCF$_3$,
(3) —$C_{3-6}$cycloalkyl, which is unsubstituted or substituted with 1-6 substituents, substituents each independently selected from:
  (a) halo,
  (b) hydroxyl,
  (c) —O—$C_{1-6}$alkyl, which is unsubstituted or substituted with 1-5 halo,
  (d) —$C_{1-6}$alkyl, which is unsubstituted or substituted with 1-5 halo, and
  (e) phenyl,
(4) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
  (a) halo,
  (b) —$C_{1-6}$alkyl, which is unsubstituted or substituted with 1-5 halo,
  (c) —O—$C_{1-6}$alkyl, which is unsubstituted or substituted with 1-5 halo,
  (d) —$C_{3-6}$cycloalkyl,
  (e) oxo,
  (f) —CN,
  (g) hydroxyl and
  (h) phenyl, and
(5) a group selected from G³;

G³ is selected from:
(1) tetrahydropyranyl, which is unsubstituted or substituted with 1-4 substitutents each independently selected from:
  (a) halo,
  (b) —OR$^a$,
  (c) —$C_{1-6}$alkyl, which is unsubstituted or substituted with 1-5 halo,
  (d) —$C_{3-6}$cycloalkyl,
  (e) —CO$_2$R$^a$,
  (f) oxo, and
  (g) phenyl,
(2) —$C_{1-6}$alkyl which is optionally substituted with 1-5 halo, but which must be further substituted with 1-4 substitutents each independently selected from:
  (a) —SR$^a$,
  (b) —S(O)$_v$R$^d$,
  (c) —NR$^a$R$^c$, (d) —OBn, which is unsubstituted or substituted with 1-5 halo,
(e) —OC(=O)$R^a$,
(f) —$CO_2R^a$,
(g) —C(=O)$NR^bR^c$,
(h) —C(=O)$R^a$,
(i) —$C_{1-6}$alkyl-O—$C_{1-6}$alkyl-$OR^a$,
(j) —N($R^a$)—C(=O)$NR^bR^c$, and
(k) —N($R^a$)—$CO_2R^d$,
(3) piperidinyl or pyrrolidinyl which is substituted with 1-4 substitutents each independently selected from:
(a) —C(=O)$R^a$,
(b) —OC(=O)$R^a$,
(c) —C(=O)$NR^bR^c$, and
(d) —S(O)$_vR^d$, $G^4$ is selected from:
(1) $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, (uranyl, imidazolidinyl, imidazolinyl, imidazolyl, indazolyl, indolinyl, indolyl, isochromanyl, isoindolinyl, isoquinolinyl, isoxazolyl, isoxazolinyl, isoxazolidinyl, isothiazolidinyl, isothiazolyl, morpholinyl, naphthyridinyl, oxadiazolyl, oxazolyl, oxazolinyl, oxazolidinyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, phthalazinyl, piperidyl, piperazinyl, pyrazinyl, pyrazolidinyl, pyrazolyl, pyridazinyl, pyridinyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, triazolyl and triazolinyl, which is unsubstituted or substituted with 1-5 substituents independently selected from $R^3$, $R^4$, $R^6$, $R^7$ and $R^8$, and
(2) a group selected from $G^1$;

$G^5$ is selected from:
(1) —$C_{1-4}$alkyl-phenyl which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(f) —S(O)$_vR^d$, and
(g) —N($R^a$)$SO_2R^d$,
(2) —$C_{1-4}$alkyl-heterocycle wherein said heterocycle is selected from pyridyl, pyrimidinyl, and indazolyl, which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(O—S(O)$_vR^d$, and
(g) —N($R^a$)$SO_2R^d$, and
(3) —$C_{1-4}$alkyl which is optionally substituted with 1-5 halo, but which must be substituted further with 1-4 substituents independently selected from:
(a) —$CO_2R^a$,
(b) —C(=O)$R^a$,
(c) —OC(=O)$R^a$,
(d) —C(=O)$NR^bR^c$,
(e) —$SR^a$,
(f) —S(O)$_vR^d$, and
(g) —N($R^a$)$SO_2R^d$;

$G^6$ is selected from
(1) hydrogen,
(2) —$C_{1-6}$alkyl, which is unsubstituted or substituted with 1-5 groups independently selected from:
(a) halo,
(b) $OR^a$,
(c) —CN, and
(d) phenyl, which is unsubstituted or substituted with 1-5 halo, and
(3) —$C_{1-6}$cycloalkyl, which is unsubstituted or substituted with 1-5 groups independently selected from:
(a) halo,
(b) $OR^a$,
(c) —CN, and
(d) phenyl, which is unsubstituted or substituted with 1-5 halo;

$R^3$, $R^4$, $R^6$, $R^7$ and $R^8$ are each independently selected from:
(1) hydrogen,
(2) —$C_{1-6}$alkyl, which is unsubstituted or substituted with 1-5 substituents each independently selected from:
(a) halo,
(b) —$OR^a$,
(c) —$C_{3-6}$cycloalkyl,
(d) phenyl or heterocycle, wherein said heterocycle is selected from: benzodioxolyl, imidazolyl, indoolyl, pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from
(i) halo,
(ii) —$C_{1-6}$alkyl, which is unsubstituted or substituted with 1-5 halo, and
(iii) —$OR^a$,
(e) —$CO_2R^a$,
(f) —C(=O)$NR^bR^c$,
(g) —S(O)$_vR^d$,
(h) —CN,
(i) —$NR^bR^c$,
(j) —N($R^b$)C(=O)$R^a$,
(k) —N($R^b$)$SO_2R^d$,
(l) —$CF_3$,
(m) —O—$CO_2R^d$,
(n) —O—(C=O)—$NR^bR^c$,
(o) —$NR^b$—(C=O)—$NR^bR^c$, and
(p) —C(=O)$R^a$,
(3) —$C_{3-6}$cycloalkyl, which is unsubstituted or substituted with 1-5 substituents each independently selected from:
(a) halo,
(b) —CN, (c) —$C_{1-6}$alkyl, which is unsubstituted or substituted with 1-5 halo,
(d) —$OR^a$, and
(e) phenyl, which is unsubstituted or substituted with 1-5 substituents each independently selected from:
 (i) —$OR^a$,
 (ii) halo,
 (iii) —CN, and
 (iv) —$C_{1-6}$alkyl, which is unsubstituted or substituted with 1-5 halo,
(4) phenyl or heterocycle, wherein said heterocycle is selected from: benzimidazolyl, benzoxazolyl, indanyl, indolyl, morpholinyl, oxadiazolyl, oxazolyl, pyridyl, pyrimidinyl, pyrazinyl, pyrazolyl, pyridazinyl, piperidinyl, piperazinyl, pyrrolidinyl, thienyl, tetrazolyl and thiazolyl, which phenyl or heterocycle is unsubstituted or substituted with 1-5 substituents each independently selected from:
(a) halo,
(b) —$OR^a$,
(c) —$C_{3-6}$cycloalkyl,
(d) phenyl or pyridyl, which is unsubstituted or substituted with 1-5 substituents each independently selected from:
 (i) halo,
 (ii) $C_{1-6}$ alkyl, which is unsubstituted or substituted with 1-6 halo, and
 (iii) —$OR^a$,
(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —O—$CO_2R^d$,
(m) —O—(C=O)—$NR^bR^c$,
(n) —$NR^b$—(C=O)—$NR^bR^c$,
(o) —$C(=O)R^a$, and
(p) —$C_{1-6}$alkyl, which is unsubstituted or substituted with 1-6 halo,
(5) halo,
(6) oxo,
(7) —$OR^a$,
(8) —CN,
(9) —$CO_2R^a$,
(10) —$C(=O)R^a$,
(11) —$NR^bR^c$,
(12) —$S(O)_vR^d$,
(13) —$C(=O)NR^bR^c$,
(14) —O—(C=O)$R^a$,
(15) —O—$CO_2R^d$,
(16) —$N(R^b)CO_2R^d$,
(17) —O—(C=O)—$NR^bR^c$,
(18) —$NR^b$—(C=O)—$NR^bR^c$,
(19) —$SO_2NR^bR^c$, and
(20) —$N(R^b)SO_2R^d$,
and $R^7$ and $R^8$ and the atom(s) to which they are attached may join to form a ring selected from azetidinyl, aziridinyl, cyclobutyl, cycloheptyl, cyclohexyl, cyclooctyl, cyclopentyl, cyclopropyl, dihydrobenzofuranyl, dihydrobenzopyranyl, dioxanyl, dioxoalanyl, indanyl, indenyl, indolinyl, isoindolinyl, morpholinyl, oxetanyl, piperazinyl, piperidinyl, pyrrolidinyl, tetrahydrofuranyl, tetrahydroisoquinolinyl, tetrahydronaphthyl, tetrahydroquinolinyl, tetrahydropyranyl, tetrahydrothiapyranyl, tetrahydrothienyl, thiamorpholinyl, and thietanyl, wherein the sulfur is optionally oxidized to the sulfone or sulfoxide, which ring is unsubstituted or substituted with 1-5 substituents each independently selected from:
(a) —$C_{1-6}$alkyl, which is unsubstituted or substituted with 1-3 substituents each independently selected from:
 (i) halo,
 (ii) —$OR^a$,
 (iii) —$C_{3-6}$cycloalkyl,
 (iv) —$CO_2R^a$,
 (v) —$NR^bR^c$,
 (vi) —$S(O)_vR^d$,
 (vii) —$C(=O)NR^bR^c$, and
 (viii) phenyl, which is unsubstituted or substituted with 1-5 halo,
(b) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-5 substituents each independently selected from:
 (i) halo,
 (ii) —$C_{1-6}$alkyl, which is unsubstituted or substituted with 1-5 halo, and
 (iii) —$OR^a$,
(c) —$OR^a$,
(d) halo,
(e) —$CO_2R^a$,
(f) —$C(=O)NR^bR^c$,
(g) —$S(O)_vR^d$,
(h) —CN,
(i) —$NR^bR^c$,
(j) —$N(R^b)C(=O)R^a$,
(k) —$N(R^b)SO_2R^d$,
(l) —O—(C=O)$R^a$,
(m) —O—$CO_2R^d$,
(n) —O—(C=O)—$NR^bR^c$,
(o) —$NR^b$—(C=O)—$NR^bR^c$,
(p) —$C(=O)R^a$, and
(q) oxo;
$R^{PG}$ is selected from:
(1) hydrogen,
(2) —$C_{1-6}$alkyl which is unsubstituted or substituted with 1-5 halo,
(3) —$CH_2OR^a$,
(4) —$CH_2$—O—$CH_2CH_2Si(CH_3)_3$,
(5) —$(CH_2)_k$-phenyl, which is unsubstituted or substituted with 1-3 substituents each independently selected from:
(a) halo,
(b) —$OR^a$,
(c) —CN, and
(d) —$C_{1-6}$alkyl, which is unsubstituted or substituted with 1-6 halo;
J is selected from:
(1) =$C(R^{16a})$—,
(2) —$CR^{17}R^{18}$—,
(3) —C(=O)—, and
(4) —$N(R^b)$—;
Y is selected from:
(1) =$C(R^{16b})$—,
(2) —$CR^{17}R^{18}$—,
(3) —C(=O)—,
(4) =N—, and
(5) —$N(R^{16b})$—;

$R^{17}$ and $R^{18}$ are each independently selected from:
(1) hydrogen,
(2) halo,
(3) —$OR^a$,
(4) —$C_{1-6}$alkyl, which is unsubstituted or substituted with 1-4 substituents each independently selected from:
 (a) halo,
 (b) —$OR^a$,
 (c) —CN,
 (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (i) —$OR^a$,
  (ii) halo,
  (iii) —CN,
  (iv) —$C_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
 (a) halo,
 (b) —CN,
 (c) —$OR^a$,
 (d) nitro,
 (e) —$C_{1-6}$alkyl which is unsubstituted or substituted with 1-6 halo;
and $R^{17}$ and $R^{18}$ and the atom to which they are attached may join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
 (a) halo,
 (b) —$OR^a$,
 (c) —$C_{1-6}$alkyl, which is unsubstituted or substituted with 1-6 halo, and
 (d) phenyl, which is unsubstituted or substituted with 1-6 halo;
$R^{16a}$ and $R^{16b}$ are each independently selected from:
(1) hydrogen,
(2) —$C_{1-4}$alkyl, which is unsubstituted or substituted with 1-5 substituents each independently selected from:
 (a) halo,
 (b) —$OR^a$,
 (c) —$C_{3-6}$cycloalkyl,
 (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
  (i) halo,
  (ii) —$OR^a$,
  (iii) —CN, and
  (iv) —$C_{1-6}$alkyl which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
 (a) halo,
 (b) —$OR^a$,
 (c) —$C_{3-6}$cycloalkyl,
 (d) —$C_{1-4}$alkyl which is unsubstituted or substituted with 1-6 halo, and
 (e) phenyl, which is unsubstituted or substituted with 1-5 substituents each independently selected from:
  (i) halo,
  (ii) —$C_{1-6}$alkyl, which is unsubstituted or substituted with 1-6 halo, and
  (iii) —$OR^a$,
(4) halo,
(5) —$OR^a$,
(6) —CN,
(7) —$CO_2R^a$,
(8) —$NR^bR^c$, and
(9) —C(=O)$NR^bR^c$;
and $R^{16a}$ and $R^{16b}$ and the atom(s) to which they are attached may join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
 (a) —$C_{1-6}$alkyl, which is unsubstituted or substituted with 1-3 substituents each independently selected from:
  (i) halo,
  (ii) —$OR^a$,
  (iii) —$C_{3-6}$cycloalkyl,
  (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
   (I) —$OR^a$,
   (II) halo,
   (III) —CN, and
   (IV) —$C_{1-6}$alkyl which is unsubstituted or substituted with 1-6 halo,
  (v) —$CO_2R^a$,
  (vi) —$NR^bR^c$,
  (vii) —$S(O)_vR^d$,
  (viii) —C(=O)$NR^bR^c$,
  (ix) —N($R^b$)$CO_2R^a$, and
  (x) —N($R^b$)$SO_2R^d$,
 (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:

(i) halo,
(ii) —OR$^a$,
(iii) —CN, and
(iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxo, and
(o) —(NR$^b$)SO$_2$R$^d$;
each R$^a$ is independently selected from:
(1) hydrogen,
(2) C$_{1-6}$alkyl, which is unsubstituted or substituted with 1-7 substituents each independently selected from:
(a) halo,
(b) —O—C$_{1-6}$alkyl, which is unsubstituted or substituted with 1-6 halo,
(c) hydroxyl,
(d) —C(=O)—O—C$_{1-6}$alkyl, which is unsubstituted or substituted with 1-6 halo,
(e) —CN, and
(f) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(i) halo,
(ii) —O—C$_{1-6}$alkyl, which is unsubstituted or substituted with 1-6 halo,
(iii) —CN,
(iv) nitro,
(v) hydroxyl, and
(vi) —C$_{1-6}$alkyl, which is unsubstituted or substituted with 1-6 halo,
(3) phenyl or heterocycle wherein said heterocycle is selected from pyridyl, indolyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(a) halo,
(b) —CN,
(c) —O—C$_{1-6}$alkyl, which is unsubstituted or substituted with 1-6 halo,
(d) nitro,
(e) hydroxyl, and
(f) —C$_{1-6}$alkyl, which is unsubstituted or substituted with 1-6 halo, and
(4) —C$_{3-6}$cycloalkyl, which is unsubstituted or substituted with 1-6 halo;
R$^b$ and R$^c$ are each independently selected from:
(1) hydrogen,
(2) C$_{1-6}$alkyl, which is unsubstituted or substituted with 1-7 substituents each independently selected from:
(a) halo,
(b) —OR$^a$,
(c) —CN,
(d) —CO$_2$R$^a$,
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(i) halo,
(ii) —OR$^a$,
(iii) —C$_{1-6}$alkyl, which is unsubstituted or substituted with 1-6 halo, and
(iv) nitro,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo,
(e) —CN, and
(f) —CO$_2$R$^a$,
(4) —C$_{3-6}$cycloalkyl, which is unsubstituted or substituted with 1-6 halo;
and R$^b$ and R$^c$ and the nitrogen to which they are attached may join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$, and
(c) —C$_{1-6}$alkyl, which is unsubstituted or substituted with 1-6 halo, and
(d) phenyl;
each R$^d$ is independently selected from:
(1) C$_{1-6}$alkyl, which is unsubstituted or substituted with 1-7 substituents each independently selected from:
(a) halo,
(b) —OR$^a$,
(c) —CO$_2$R$^a$
(d) —CN, and
(e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydropyranyl, tetrahydropyranyl and pyrazinyl, which phenyl or heterocycle is unsubstituted or substituted with 1-3 substituents each independently selected from:
(i) halo,
(ii) —OR$^a$,
(iii) —CN,
(iv) nitro, and
(v) —C$_{1-6}$alkyl, which is unsubstituted or substituted with 1-6 halo,
(2) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:

(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo
(e) nitro,
(f) —CN, and
(g) —CO$_2$R$^a$, (3) —C$_{3-6}$cycloalkyl, which is unsubstituted or substituted with 1-6 halo;

m is 1, 2, or 3;
n is 1, 2, or 3;
v is 0, 1, or 2;
k is 0, 1, or 2;

and pharmaceutically acceptable salts thereof.

2. The compound of claim 1 wherein m is 1 and n is 1.

3. The compound of claim 1 having the formula Ia

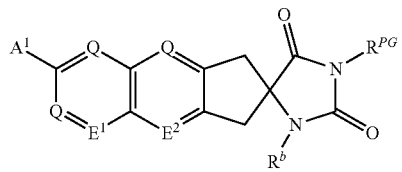

and pharmaceutically acceptable salts thereof.

4. The compound of claim 1 having the formula Ib

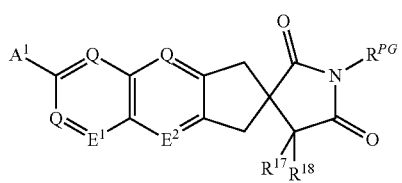

and pharmaceutically acceptable salts thereof.

5. The compound of claim 1 having the formula Ic

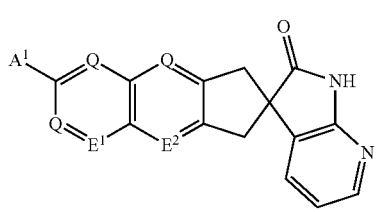

and pharmaceutically acceptable salts thereof.

6. The compound of claim 1 having the formula Id

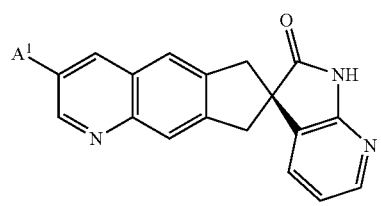

and pharmaceutically acceptable salts thereof.

7. The compound according to claim 6 wherein A$^1$ is

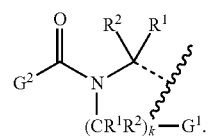

8. The compound according to claim 6 wherein A$^1$ is

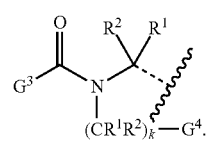

9. The compound according to claim 6 wherein A$^1$ is

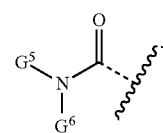

10. The compound of claim 1 having the formula Ie

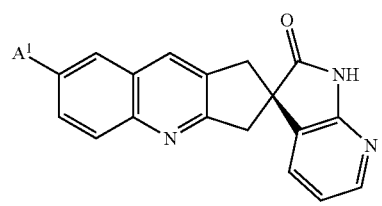

and pharmaceutically acceptable salts thereof.

11. The compound according to claim 10 wherein A$^1$ is

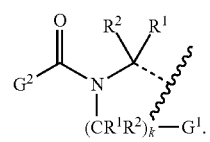

12. The compound according to claim 10 wherein $A^1$ is

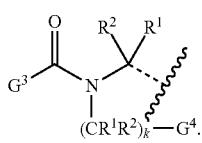

13. The compound according to claim 10 wherein $A^1$ is

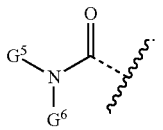

14. A compound according to claim 1 selected from the following:

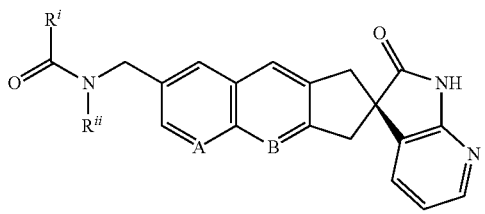

| $R^i$ | $R^{ii}$ | A | B |
|---|---|---|---|
| Tetrahydro-2H-pyran-4-yl | (1R)-1-(3,5-difluorophenyl)ethyl | N | CH |
| 2-ethoxy-2-oxoethyl | Benzyl | N | CH |
| tetrahydro-2H-pyran-4-yl | (1R)-2,3-dihydro-1H-inden-1-yl | N | CH |
| tetrahydro-2H-pyran-4-yl | (1R)-1-(3-chlorophenyl)ethyl | N | CH |
| tert-butyl | tetrahydro-2H-thiopyran-4-yl | N | CH |
| tetrahydro-2H-pyran-4-yl | cycloheptyl | N | CH |
| tetrahydro-2H-pyran-3-yl | (1R)-1-(3,5-difluorophenyl)ethyl | N | CH |
| tetrahydro-2H-pyran-4-yl | 3,5-dichlorobenzyl | N | CH |
| tetrahydro-2H-pyran-4-yl | 3-fluorobenzyl | N | CH |
| tetrahydro-2H-pyran-2-yl | 3-fluorobenzyl | N | CH |
| 1-(acetyloxy)-1-methylethyl | (1R)-2,3-dihydro-1H-inden-1-yl | N | CH |
| Tert-butyl | tetrahydro-2H-pyran-4-yl | N | CH |
| (1S)-1-(benzyloxy)-2,2,2-trifluoro-1-methylethyl | (1R)-1-(3,5-difluorophenyl)ethyl | N | CH |
| (1S)-1-(benzyloxy)-2,2,2-trifluoro-1-methylethyl | (1R)-2,3-dihydro-1H-inden-1-yl | N | CH |
| (1S)-1-(benzyloxy)-2,2,2-trifluoro-1-methylethyl | 3-fluorobenzyl | N | CH |
| tetrahydro-2H-pyran-4-yl | [1-(tert-butoxycarbonyl)-4-phenylpyrrolidin-3-yl] | N | CH |
| 2-(methylthio)ethyl | 3-fluorobenzyl | N | CH |
| 2-thienylmethyl | 3-fluorobenzyl | N | CH |
| 3-methoxy-3-oxopropyl | 3-fluorobenzyl | N | CH |
| (2-methoxyethoxy)methyl | 3-fluorobenzyl | N | CH |
| tetrahydro-2H-pyran-4-yl | cis-2-phenylcyclopentyl | N | CH |
| tetrahydro-2H-pyran-4-yl | trans-2-phenylcyclopentyl | N | CH |
| tetrahydro-2H-pyran-4-yl | cis-2-(4-chlorophenyl)cyclopentyl | N | CH |
| 2-ethoxy-2-oxoethyl | 3-fluorobenzyl | N | CH |
| 1-(acetyloxy)ethyl | (1R)-2,3-dihydro-1H-inden-1-yl | N | CH |
| 1-(acetyloxy)-1-methylethyl | (1R)-2,3-dihydro-1H-inden-1-yl | CH | N |
| (dimethylamino)methyl | 3-fluorobenzyl | N | CH |

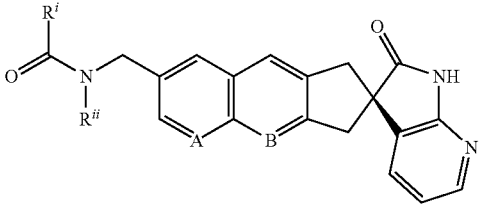

| $R^i$ | $R^{ii}$ | A | B |
|---|---|---|---|
| tetrahydro-2H-pyran-4-yl | (1S,2S)-2-(benzyloxy)cyclopentyl | N | CH |
| tetrahydro-2H-pyran-4-yl | (1R,2R)-2-(benzyloxy)cyclopentyl | N | CH |
| tetrahydro-2H-pyran-4-yl | 4-phenylpyrrolidin-3-yl | N | CH |
| 1-(acetyloxy)-1-methylethyl | (1R)-2,3-dihydro-1H-inden-1-yl | CH | N | and pharmaceutically acceptable salts of any of the foregoing compounds.

15. A compound according to claim 1 selected from the following:

| $R^{iii}$ | $R^{iv}$ |
|---|---|
| 2-tert-butoxy-2-oxoethyl | Bn |
| (1R)-2-tert-butoxy-2-oxo-1-phenylethyl | H |
| (1S)-2-tert-butoxy-2-oxo-1-phenylethyl | H |
| 2-methoxy-1-[(7-methyl-1H-indazol-5-yl)methyl]-2-oxoethyl | H |
| 3-tert-butoxy-3-oxo-1-phenylpropyl | H |
| 1-benzyl-2-tert-butoxy-2-oxoethyl | H | and pharmaceutically acceptable salts of any of the foregoing compounds.

16. A pharmaceutical composition which comprises an inert carrier and the compound of claim 1.

17. A method for antagonism of CGRP receptor activity in a mammal which comprises the administration of an effective amount of the compound of claim 1.

18. A method for treating, headache, migraine or cluster headache in a mammalian patient in need of such which comprises administering to the patient a therapeutically effective amount of the compound of claim 1.

19. A method of treating migraine headaches, cluster headaches, and headaches, said method comprising the co-administration, to a person in need of such treatment, of:
 a therapeutically effective amount of the compound of claim 1 or a pharmaceutically acceptable salt thereof; and
 a therapeutically effective amount of a second agent selected from serotonin agonists, analgesics, anti-inflamatory agents, anti-hypertensives and anticonvulsants.

\* \* \* \* \*